United States Patent [19]

Matsuoka et al.

[11] Patent Number: 4,992,173
[45] Date of Patent: Feb. 12, 1991

[54] BOILER OPERATING METHOD WITH GASES PRODUCED FROM BIOREACTOR

[75] Inventors: Keiji Matsuoka, Kani; Yuzo Okamoto, Nagoya; Isao Niwa, Gifu, all of Japan

[73] Assignee: NGK Insulators, Ltd., Japan

[21] Appl. No.: 524,796

[22] Filed: May 18, 1990

[30] Foreign Application Priority Data

May 19, 1989 [JP] Japan ................................ 1-127475

[51] Int. Cl.$^5$ ................................ C02F 3/28
[52] U.S. Cl. ................................ 210/603; 210/612; 210/774; 48/197 A
[58] Field of Search ............... 210/603, 612, 613, 614, 210/742, 744, 774, 96.1, 180; 48/197 A; 435/316; 165/1, 32

[56] References Cited

U.S. PATENT DOCUMENTS

| | | | |
|---|---|---|---|
| 3,981,803 | 9/1976 | Coulthard | 210/180 |
| 4,013,516 | 3/1977 | Greenfield et al. | 210/774 |
| 4,046,551 | 9/1977 | Anderson | 48/197 A |
| 4,198,292 | 4/1980 | Snider et al. | 210/612 |
| 4,246,099 | 1/1981 | Gould et al. | 210/603 |
| 4,551,243 | 11/1985 | Martin | 210/180 |

Primary Examiner—Tom Wyse
Attorney, Agent, or Firm—Parkhurst, Wendel & Rossi

[57] ABSTRACT

A method is for operating a boiler to heat a bioreactor with gases produced from the bioreactor, while supplying excessive hot water to outside of a system. In the method, the boiler is operated to turn on and off depending upon temperature of a hot water tank when a level of a gas holder is higher than an intermediate level $H_1$. Hot water is unconditionally supplied to the outside of the system when the level of the gas holder is higher than a high level $H_2$, and hot water is supplied to the outside when temperature of the hot water tank is higher than an intermediate temperature $L_1$ and the level of the gas holder is between the high level $H_2$ and the intermediate level $H_1$. The supply of the hot water is stopped when the level of the gas holder is less than the intermediate level $H_1$.

2 Claims, 1 Drawing Sheet

BOILER OPERATING METHOD WITH GASES PRODUCED FROM BIOREACTOR

BACKGROUND OF THE INVENTION

This invention relates to a method of operating a boiler with gases produced from a bioreactor for anaerobic treatment.

In general, combustible digestion gases are produced from a bioreactor for anaerobic treatment owing to decomposition of organic substances. A calorific value of the gases with a bioreactor having a capacity of 50 m$^3$ attends as much as 3,600,000 Kcal per day which corresponds to that of approximately 400 liters of heavy oil. On the other hand, this kind of bioreactor usually requires to be heated so that the bioreactor is heated by hot water obtained when the boiler is operated by the produced gases above described.

With such a system, a calorific value of the produced gases under designed loaded conditions is generally more than that required for heating the bioreactor so that the system is constructed to supply the excessive heat as hot water to outside of the system. If an actual load is less than the designed load, the calorific value of the produced gases often becomes insufficient. With the system of the prior art, however, the system would continue supplying the hot water to the outside so that a large amount of heat must be supplied to the bioreactor from an external heat source with steam or the like. Therefore, it is disadvantageous in the viewpoint of effective use of the entire heat.

SUMMARY OF THE INVENTION

It is a primary object of the invention to provide a method of operating a boiler with gases produced from a bioreactor, which eliminates all the diadvantages of the prior art and enable a system to be operated without supplying heat from an external heat source as far as possible even if change in treated amount of drainage of the bioreactor takes place and further which is able to effectively supply excessive heat as hot water if any to outside of the system.

In order to accomplish this object of the invention, in the method of operating a boiler for heating a bioreactor with gases produced from the bioreactor, while supplying excessive hot water to outside of a system according to the invention, the boiler is operated to turn on and off depending upon temperature of a hot water tank when a level of a gas holder is higher than an intermediate level $H_1$, and hot water is unconditionally supplied to the outside when the level of the gas holder is higher than a high level $H_2$, and hot water is supplied to the outside when temperature of the hot water tank is higher than an intermediate temperature $L_1$ and the level of the gas holder is between the high level $H_2$ and the intermediate level $H_1$ and the supply of the hot water is stopped when the level of the gas holder is less than the intermediate level $H_1$.

The invention will be more fully understood by referring to the following detail specification and claims taken in connection with the appended drawings.

EXPLANATION OF THE PREFERRED EMBODIMENT

Figure 1:
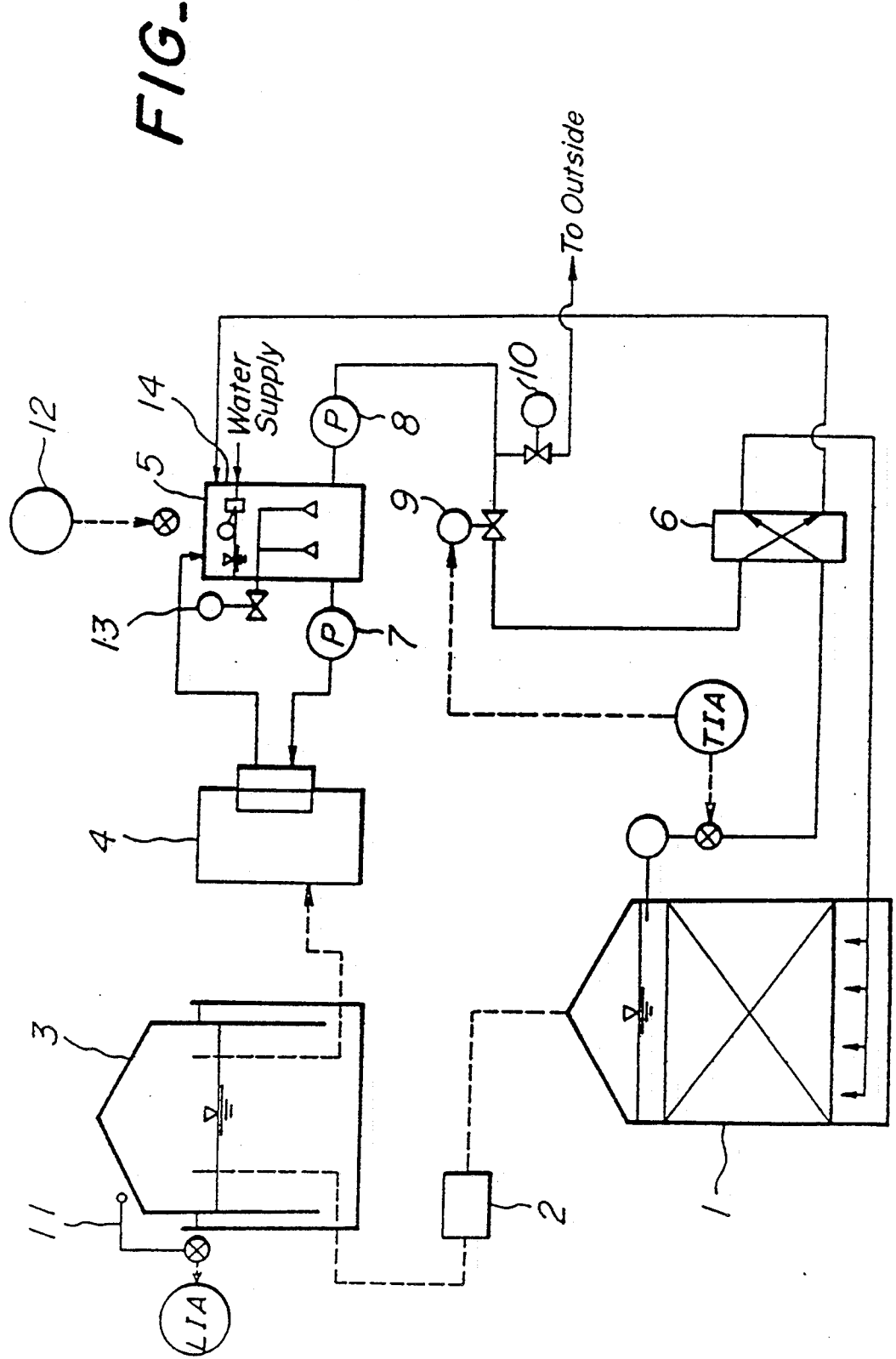
FIG. 1 is a drawing illustrating a control system for explaining one embodiment of the method according to the invention.

FIG. 1 illustrates a system for carrying out the method according to the invention, which comprises a bioreactor 1 for anaerobic treatment, a purifier 2, a gas holder 3 for reserving desulfurized produced gases, a boiler 4 for heating the bioreactor 1, a hot water tank 5 for storing hot water obtained from the boiler 4 and a heat exchanger 6. FIG. 1 further illustrates a first pump 7 provided between the hot water tank 5 and the boiler 4, a second pump 8 provided on an outlet side of the hot water tank 5, a first valve 9 provided between an outlet of the hot water tank 5 and the heat exchanger 6 and a second valve 10 for supplying the hot water in the hot water tank 5 to the outside of the system. The first valve 9 is adapted to open to feed the hot water into the heat exchanger 6 when heating the bioreactor 1.

The gas holder 3 is provided with a level gauge 11 which emits level signals for five levels, for example, a superhigh level Hh, a high level $H_2$, an intermediate level $H_1$, a low level $L_1$ and a superlow level $L_2$. Moreover, the hot water tank 5 is provided with a thermometer 12 adapted to emit temperature signals for five levels, for example, a superhigh temperature HH, a high temperature H, an intermediate temperature $L_1$, a low temperature $L_2$ and a superlow temperature LL.

With such a system, the superhigh level HH, the superlow level $L_2$ and superhigh temperature HH are alarm levels.

The operating conditions of the system will be progressively explained hereinafter. First, the boilder 4 is operated to be turned on and off depending upon the temperature in the hot water tank 5 when the level of the gas holder 3 is higher than the intermediate level $H_1$. That is to say, the boiler 4 is turned off when the temperature of the hot water tank 5 beocmes the high temperature H, while the boiler 4 is turned on when the temperature of the hot water tank 5 lowers to the low temperature $L_2$. When the boiler 4 is on, the first pump 7 is naturally on also, thereby maintaining the temperature in the hot water tank 5 within a suitable temperature range.

Moreover, the boiler 4 is inoperative when the level of the gas holder 3 is lower tan the low level $L_1$. When the temperature in the bioreactor 1 lowers owing to the inoperative boiler 4 and the temperature of the hot water tank 5 lowers to be lower than the superlow temperature LL, heat supply from an external heat source is unavoidably necessary. In this embodiment, an automatic control system is incorporated in the system so that a steam valve 13 is opened when the temperature of the hot water tank is the temperature LL, and the steam valve 13 is closed when the temperature of the hot water tank attends the temperature H.

The second valve 10 for supplying hot water to the outside of the system is turned on and off depending upon the level of the gas holder 3 and the temperature of the hot water tank 5 in the following manner.

First, when the level of the gas holder 3 is higher than the high level $H_2$, the second valve 10 is unconditionally turned on to supply the hot water to the outside of the system.

Upon supplying the hot water to the outside of the system, the water level of the hot water tank lowers. When the level of the hot water tank lowers, cold water (at ordinary room temperature) is supplied into the hot water tank so taht the temperature of the hot water tank will lower. The temperature of the hot water tank lowers to the temperature $L_2$ at which time the boiler is turned on and the second valve 10 is closed, with the result that the level of the gas holder is lowered, and supply of hot water to the outside of the system more than required is prevented.

When the level of the gas holder 3 is between the high level $H_2$ and the intermediate level $H_1$, the second valve 10 is opened to supply the hot water to the outside of the system but only insofar the temperature in the hot water tank 5 is higher than the intermediate temperature $L_1$.

Moreover, when the level of the gas holder is lower than the intermediate level $H_1$, the supply of the hot water to the outside of the system is stopped irrespective of the temperature of the hot water tank 5.

The actual operation of the system will be explained.

(1) A case that calorific value of the boiler is more than quantity of heat required for heating a bioreactor In this case, the level of the gas holder 3 is raised or lowered between the high level $H_2$ and the intermediate level $H_1$ and the second valve 10 is opened and closed so that the hot water is supplied to the outside of the system every time when the second valve 10 is opened. In more detail, when the level of the gas holder 3 attends the high level $H_2$, the second valve 10 is unconditionally opened to supply the hot water to the outside of the system. As a result, the hot water tank 5 is replenished with water so that the temperature of the hot water tank 5 lowers. When the temperature of the hot water tank 5 lowers to the low temperature $L_2$, the supply of the water to the hot water tank 5 is stopped and the boiler 4 is turned on so that the level of the gas holder 3 begin to lower progressively from the higher level $H_2$. However, when the level of the gas holder 3 is between the high level $H_2$ and the intermediate level $H_1$, the temperature of the hot water tank again rises. When the temperature of the hot water tank attends a temperature higher than the intermediate temperature $L_1$, the second valve 10 is opened to supply hot water to the outside of the system.

The hot water is intermittently supplied to the outside from the hot water tank 5 whose temperature rises and lowers between the intermediate temperature $L_1$ and the low temperature $L_2$ in this manner. If the temperature of the hot water tank 5 becomes the high temperature H, the boiler 4 becomes off or inoperative. At this moment, the level of the gas holder 3 rises to the high level $H_2$ so that the hot water is supplied to the outside of the system from the hot water tank 5. As a result, the boiler 4 is turned on. The level of the gas holder 3 continues to lower until the boiler 4 becomes off or inoperative. When the level of the gas holder 3 becomes less than the intermediate level $H_1$, the supply of the hot water to the outside of the system is stopped irrespective of the temperature of the hot water tank 5.

If the temperature in the bioreactor 1 lowers, the first valve 9 is opened to feed the hot water from the hot water tank 5 into the heat exchanger 6. However, as the calorific value of the heat from the boiler 4 is more than the quantity of heat required for heating the bioreactor, the level of the gas holder 3 starts to rise surely on stopping the supply of the hot water to the outside of the system. Thereafter, the system is operated in the similar manner.

(2) A case that calorific value of the boiler is less than quantity of heat required for heating a bioreactor In actual, the level of the gas holder 3 changes between the intermediate level $H_1$ and the low level $L_1$ and the supply of the hot water to the outside of the system is not effected. In other words, the hot water is fed from the hot water tank 5 into the heat exchanger 6 in order to heat the bioreactor 1. When the temperature of the hot water tank 5 lowers to the low temperature $L_2$, the boiler becomes on or operative. After a while. when the temperature of the hot water tank 5 becomes the high temperature H, the boiler 4 is turned off or inoperative. The level of the gas holder 3 progressively lowers to the low level $L_1$ in this manner until the operation of the boiler becomes impossible. Therefore, it is necessary to heat the bioreactor by supplying steam or the like from an external heat source.

As above explained, according to the invention even if the calorific value of the boiler is more than the quantity of heat required for heating the bioreactor so that excessive hot water can be supplied to the outside of the system, the level of the gas holder is maintained higher than the intermediate level $H_1$ to insure reserving the quantity of heat for heating the bioreactor. Therefore, the invention can completely prevent such a useless energy consumption due to fuel supply from an external heat source to the boiler as a result that the supply of the hot water to the outside of the system is continued irrespective of the level of the gas holder as in the prior art.

According to the invention, moreover, in case that calorific value of the boiler is less than quantity of heat required for heating the bioreactor, the supply of the hot water to the outside of the system is not carried out so that 100% of the quantity of heat produced from the bioreactor can be utilized for heating the bioreactor.

As can be seen from the above explanation, according to the invention the supply of the hot water to the exterior is performed only when quantity of heat becomes completely excessive irrespective of amount of produced gases. Therefore, the system can be operated without supplying heat from an external heat source as far as possible even if drain treatment amount of the bioreactor changes. Therefore, the invention greatly contribute to the improvement of industries as a method of operating a boiler with gases produced from a bioreactor, which solves the problems of the prior art.

While the invention has been particularly shown and described with reference to preferred embodiments thereof, it will be understood by those skilled in the art than the foregoing and other changes in form and details can be made therein without departing from the spirit and scope of the invention.

What is claimed is:

1. A method of operating a boiler for heating a bioreactor with gases produced from the bioreactor, while supplying excessive hot water to outside of a system wherein the boiler is operated to turn on and off depending upon temperature of a hot water tank when a level of a gas holder is higher than an intermediate level $H_1$, and hot water is unconditionally supplied to the outside when the level of the gas holder is higher than a high level $H_2$, and hot water is supplied to the outside when temperature of the hot water tank is higher than an intermediate temperature $L_1$ and the level of the gas holder is between the high level $H_2$ and the intermediate level $H_1$ and the supply of the hot water is stopped when the level of the gas holder is less than the intermediate level $H_1$.

2. A method as set forth in claim 1, wherein the temperature of the hot water tank is divided into five steps, a superhigh temperature HH, a high temperature H, an intermediate temperature $L_1$, a low temperature $L_2$ and a superlow temperature LL, and the boiler is turned off when the temperature of the hot water tank rises to the high temperature H, and the boiler is turned on when the temperature of the hot water tank lowers to the low temperature $L_2$.

* * * * *